United States Patent
Simonato et al.

(10) Patent No.: US 6,946,574 B2
(45) Date of Patent: Sep. 20, 2005

(54) METHOD FOR PREPARING CARBOXYLIC ACIDS BY PALLADIUM CARBONYLATION

(75) Inventors: Jean-Pierre Simonato, Sassenage (FR); Pascal Metivier, Lyons (FR)

(73) Assignee: Rhodia Polyamide Intermediates, Saint Fons (FR)

( * ) Notice: Subject to any disclaimer, the term of this patent is extended or adjusted under 35 U.S.C. 154(b) by 0 days.

(21) Appl. No.: 10/451,662

(22) PCT Filed: Dec. 21, 2001

(86) PCT No.: PCT/FR01/04149
§ 371 (c)(1),
(2), (4) Date: Nov. 6, 2003

(87) PCT Pub. No.: WO02/051783
PCT Pub. Date: Jul. 4, 2002

(65) Prior Publication Data
US 2004/0068142 A1 Apr. 8, 2004

(30) Foreign Application Priority Data
Dec. 27, 2000 (FR) .......................... 00 17101

(51) Int. Cl.⁷ .............................. C07C 57/02
(52) U.S. Cl. ............. 562/598; 562/522; 562/546; 502/34
(58) Field of Search ................. 562/522, 406, 562/497, 221, 517; 568/420, 651, 456, 482; 502/20, 34, 53, 27, 28

(56) References Cited

U.S. PATENT DOCUMENTS

| | | | |
|---|---|---|---|
| 3,509,209 A | | 4/1970 | Fenton et al. |
| 4,568,653 A | * | 2/1986 | Schwirten et al. ............ 502/34 |
| 5,041,642 A | | 8/1991 | Jenck |
| 5,625,096 A | | 4/1997 | Denis et al. |
| 5,981,788 A | * | 11/1999 | Ofori et al. ................. 558/274 |

FOREIGN PATENT DOCUMENTS

| | | |
|---|---|---|
| EP | 0 648 731 B1 | 1/1998 |
| FR | 2 529 885 A1 | 7/1982 |
| GB | 655339 | 7/1951 |

* cited by examiner

Primary Examiner—Johann Richter
Assistant Examiner—Karl Puttlitz
(74) Attorney, Agent, or Firm—Burns, Doane, Swecker & Mathis, LLP

(57) ABSTRACT

The present invention relates to a process for the preparation of β- or γ-unsaturated or saturated carboxylic acids.

It relates more particularly to the hydroxycarbonylation of an organic compound comprising a conjugated unsaturation, such as butadiene, by the action of carbon monoxide and water in the presence of a palladium-based catalyst. The carboxylic acids thus obtained are preferably pentenoic acids. According to the invention, the reaction medium after the end of the hydroxycarbonylation stage is treated with hydrogen to reduce the palladium present in the 2+ oxidation state to palladium in the zero oxidation state and the precipitated palladium is recovered.

14 Claims, No Drawings

METHOD FOR PREPARING CARBOXYLIC ACIDS BY PALLADIUM CARBONYLATION

The present invention relates to a process for the preparation of β- or γ-unsaturated or saturated carboxylic acids.

It relates more particularly to the hydroxycarbonylation of an organic compound comprising a conjugated unsaturation, such as butadiene, by the action of carbon monoxide and water in the presence of a palladium-based catalyst. The carboxylic acids thus obtained are preferably pentenoic acids.

One of the possible routes of access to adipic acid, which is one of the two basic constituents of polyamides, such as polyamide 6,6, is the double carbonylation of butadiene or its derivatives.

Although it is possible to imagine carrying out the two hydroxycarbonylations leading from butadiene to adipic acid in a single stage, it turns out in practice that the two reactions have to be carried out successively if it is desired to obtain selectivities which are sufficiently high to be able to envisage an economically viable industrial process.

U.S. Pat. No. 3,509,209 discloses the hydroxycarbonylation of various olefins, including butadiene, by carbon monoxide and water in the presence of hydrochloric acid or hydrobromic acid and of a palladium-comprising catalyst at a temperature of 15° C. to 300° C. and under a pressure of 1 to 1 000 bar, preferably of 10 to 200 bar.

Under the conditions described, it is observed that the yields of pentenoic acids are very low and that, in reality, the product obtained is very often valerolactone.

Patent FR-A-2 529 885 has provided a process for the preparation of β- or γ-unsaturated acids, such as pentenoic acids, by carbonylation of a conjugated diene (more particularly butadiene) in the presence of water, of a hydrohalic acid, of a palladium-based catalyst and of a quaternary onium salt, the onium being that of an element chosen from nitrogen, phosphorus and arsenic.

This process gives good results but it requires the use of a relatively large amount of a quaternary onium salt, which is an expensive compound and one whose presence is of such a nature as to complicate the treatment of the mixtures at the end of the reaction.

European Patent 0 648 731 also discloses a process for the hydroxycarbonylation of butadiene and its derivatives to pentenoic acids in the presence of crotyl chloride, in the proportion of at least two mol per mole of palladium, the palladium being at least partially in the form of a π-crotyl complex. This process makes it possible to avoid the use of onium salt.

These various processes make possible the manufacture of carboxylic acids with acceptable yields and selectivities. However, the recovery and the recycling of the catalyst has never been described in these documents. As the metal used is a precious metal, the partial recovery of this catalyst does not allow an industrial development of these processes.

One of the aims of the present invention is to provide a hydroxycarbonylation process comprising a complete or substantially complete recovery of the palladium catalyst. Furthermore, the invention provides a recovery of the palladium which makes possible recycling of the latter in a further hydroxycarbonylation stage.

To this end, the invention provides a process for the manufacture of β- or γ-unsaturated carboxylic acids or of saturated carboxylic acids by reaction, with carbon monoxide and water, of a compound comprising an ethylenic or acetylenic unsaturation conjugated with another unsaturation or an electron-donating group carried by the carbon in the position α to the said unsaturation. This reaction is carried out in the presence of a palladium-based catalyst which is soluble in the medium.

The process of the invention is characterized in that the reaction medium, at the end of the hydroxycarbonylation reaction, is treated in a first stage, in order to extract the carbon monoxide present in the medium by evaporation or entrainment of the CO, and then in a second stage, in order to reduce the palladium present in the medium to palladium in the zero oxidation state by treatment with hydrogen. The palladium thus reduced precipitates and can be separated from the reaction medium by conventional solid/liquid separating means.

According to one characteristic of the invention, the concentration of CO in the medium before treatment with hydrogen is advantageously less than 600 ml of CO per litre of solution, preferably less than 100 ml of CO per litre of solution. The concentration of CO is also preferably greater than 0.001 ml of CO per litre of solution.

The term "compounds comprising an unsaturation" should be understood as meaning the compounds of general formulae:

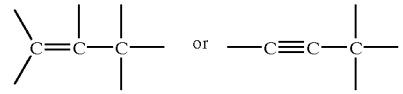

in which the carbon in the α position with respect to the ethylenic or acetylenic unsaturation also carries an ethylenic unsaturation or an electron-donating radical, such as, for example, halogen atoms, substituted or unsubstituted amino groups, or alkoxy, hydroxyl, oxo, epoxy, carbonyl, mercaptoalkyl, ester and/or cyano groups.

Mention may be made, as examples of such unsaturated compounds, of diolefins, allyl alcohols, allyl ethers, allyl esters and allyl halides.

The preferred compound of the invention is butadiene, which makes possible the manufacture of pentenoic acids by simple hydroxycarbonylation or adipic acid by double hydroxycarbonylation.

The catalyst of the invention is a palladium compound which is soluble in the reaction medium. The compounds for the implementation of the invention are those described in the documents cited above to illustrate the state of the art.

Mention may be made, for example, of palladium compounds comprising one or more anionic groups, such as, for example, those derived from hydrochloric, hydriodic, hydrofluoric or hydrobromic acids, sulphuric acid, nitric acid or carbonic acid.

Anionic groups derived from sulphonic acids, thioalcohols or carboxylic acids, such as acetic acid, propionic acid or pivalic acid, or the like, are also suitable.

Use may also be made of complexes formed from compounds comprising phosphorus or nitrogen atoms.

The palladium can also be present in the form of organic complexes, which can be formed before the introduction into the reaction medium or directly in the said medium.

Examples of complexes which can be used in the present process are: bis(π-allylpalladium chloride), bis(π-allylpalladium bromide), acetylacetonato(allyl)palladium, bis(π-isobutenylpalladium chloride), bis(π-cyclohexenylpalladium chloride) and other π-allyl complexes, such as bis(π-4-chlorocrotylpalladium chloride) and bis(π-2-methyl-4-chlorocrotylpalladium chloride), π-allylcarbonylpalladium chlorides and π-isobutenylcarbonylpalladium chloride, respectively, for example ($C_4H_7Pd_2Cl_2CO)_2$), and, furthermore, ethylenepalladium chloride.

It is also possible to use organic palladium complexes, such as palladium acetylacetonate, bis(bibenzylideneacetone)palladium, the dimer of palladium crotyl chloride, or complexes of aromatic or aliphatic phosphines with palladium, such as tetrakis(triphenylphosphine)palladium or bis(triphenylphosphine)palladium dichloride.

According to a preferred embodiment of the invention, the palladium catalyst is formed in situ by addition of crotyl chloride, in a proportion of at least two mol per mole of palladium. The palladium is thus at least partially in the form of a π-crotyl complex, as disclosed in European Patent No. 0 648 731.

According to the invention, the process for the hydroxycarbonylation of unsaturated organic compounds described above, which compounds will be exemplified for more clarity with reference to butadiene, by carbon monoxide and water is advantageously carried out at a carbon monoxide pressure greater than atmospheric pressure.

Advantageously, the water present in the reaction medium represents an amount of less than or equal to 20% by weight with respect to the weight of the reaction mixture.

The term "butadiene derivative" is understood to mean, in the present text, in particular allylic butenols, such as 3-buten-2-ol, 2-buten-1-ol and their mixtures, or addition compounds of hydrogen chloride with butadiene (chlorobutenes), the main one of which is crotyl chloride.

In the present process, it is possible to employ butadiene, one or more of its derivatives or mixtures of butadiene with one or more of its derivatives. Butadiene or mixtures predominantly comprising butadiene represent, however, the preferred substrates.

The π-crotylpalladium complex catalyst can be introduced into the reaction medium or can be formed in situ from Pd halides, more particularly the chloride, from Pd carboxylates, in particular the acetate, or from finely divided palladium metal.

The amount of π-crotylpalladium catalyst used in the process can vary within wide limits. Generally, from $10^{-5}$ mol to 0.2 mol of Pd is employed per mole of butadiene or of butadiene derivative charged to the reaction and preferably from $10^{-4}$ mol to 0.1 mol per mole.

In addition to the π-crotylpalladium catalyst, palladium can also be found in the reaction medium in another less active form (for example, Pd metal or Pd chloride) in a variable amount. In an industrial process, it is, however, preferable for all or virtually all the palladium to be in an active form which is soluble in the medium, such as π-crotylpalladium, optionally with palladium chloride.

The π-crotylpalladium complex can be prepared, for example, by reacting a palladium salt, such as palladium chloride, with crotyl chloride in a solvent which can be composed of a water/methanol mixture. The mixture is stirred, generally at ambient temperature, advantageously under a gentle stream of carbon monoxide. The π-crotylpalladium complex precipitates. After an optional degassing phase, the mixture is poured into water and is then extracted using a suitable organic solvent, such as, for example, chloroform. The complex is subsequently isolated from the organic solution by evaporation of the solvent.

The crotyl chloride promoter may be introduced into the reaction mixture or can be formed in situ from butadiene and/or 2-buten-1-ol and hydrochloric acid.

It preferably represents, as mole per mole, from 5 to 10 times the amount of palladium, although it can be present in larger proportions, since it can constitute all or part of the substrate to be hydroxycarbonylated.

Taken as a whole, it is preferable to have, in the reaction medium, a Cl/Pd molar ratio of less than or equal to 100 and preferably of less than or equal to 20, as high ratios have a harmful effect on the kinetics of the reaction.

As indicated above, the concentration of water in the reaction mixture is advantageously maintained at a value equal to or less than 20% by weight with respect to the weight of the said mixture. This is because the concentration of water has an effect on the kinetics of the reaction. This concentration of water will preferably be maintained at a value of equal to or less than 8% by weight and more preferably still at a value of equal to or less than 5%.

As water is an essential reactant in the hydroxycarbonylation reaction, an advantageous alternative form of the process of the invention consists in injecting this water as the reaction progresses, which makes it possible to maintain its concentration in the reaction mixture at a very low value while making it possible for the reaction to be carried out.

Although the presence of a third solvent is not excluded, the reaction is generally carried out without a solvent other than the reactants themselves or the reaction products. It can also be favourable to introduce, from the beginning of the hydroxycarbonylation reaction, a pentenoic acid and more particularly penten-3-oic acid, in order to minimize side reactions.

In the context of an industrial implementation of the process, operations in which the unreacted butadiene is recycled can lead to the introduction, into the reaction medium, of more or less significant amounts of other compounds, in particular byproducts formed during the hydroxycarbonylation reaction. Thus, it is possible to have, in the reaction mixture, butenes, γ-valerolactone, valeric acid, adipic acid, 2-methylglutaric acid, 2-ethylsuccinic acid, 2-methylbutanoic acid or 2-methylbutenoic acids, for example. In view of the requirements of a possible continuous implementation of the process, the amounts of these compounds present can reach up to 90% by weight of the reaction mixture charged to the hydroxycarbonylation reaction.

The concentration of butadiene is a significant reaction parameter, in particular as regards the stability of the palladium catalyst, that is to say essentially its maintenance in solution in the reaction mixture. It has thus been observed that it is unfavourable to have less than 0.2% by weight of butadiene with respect to the total weight of the reaction mixture. Preferably, when the reaction is carried out batchwise, the conversion of the butadiene or its derivatives will be limited so that the reaction mixture includes at least 0.5% by weight of the said butadiene or its derivatives.

The concentration of butadiene will also preferably be maintained at a value of less than or equal to 50% as weight by weight of the reaction mixture and more preferably still at a value of equal to or less than 30%, when the reaction is carried out in a batchwise process, and at a value of equal to or less than 10%, when the reaction is carried out in a continuous process.

The embodiment of the hydroxycarbonylation process described above exhibits the advantage, with respect to other embodiments, of keeping the palladium in solution in the reaction medium up to the end of the reaction, making it possible to maintain high kinetics.

The hydroxycarbonylation reaction can be carried out at a temperature generally situated between 60° C. and 230° C. and preferably between 90° C. and 200° C. and under a pressure, at the temperature, of 50 to 500 bar and preferably from 100 to 300 bar.

The carbon monoxide partial pressure, measured at 25° C., is from 25 bar to 440 bar and preferably from 55 bar to 240 bar.

As has been indicated, the process of the invention can be carried out continuously or batchwise. There will therefore be good reason to adjust the various operating conditions defined above according to the implementation chosen.

The reaction medium obtained at the end of the hydroxycarbonylation reaction comprises palladium in the dissolved form.

The invention provides a treatment of this reaction medium which makes it possible to recover palladium in the insoluble form with a degree of recovery of approximately 100%.

This treatment consists, in a first stage, in extracting the carbon monoxide dissolved in the reaction medium. This extraction can be obtained by heating the medium with an atmosphere not comprising CO. More advantageously, this extraction is carried out by placing the reaction medium under an inert or hydrogen atmosphere, optionally with sparging of this inert gas or hydrogen into the reaction medium. The term "inert gas" is understood to mean nitrogen or the rare gases.

This stage can be carried out at a temperature of between 20° C. (ambient temperature) and 150° C.

This operation is carried out to extract virtually all the carbon monoxide which can be extracted from the reaction medium. Thus, the concentration of carbon monoxide in the reaction medium can advantageously be less than 600 ml/l, preferably less than 100 ml/l, of solution. Advantageously, the concentration of CO in the reaction medium is between 0.001 ml/l and 600 ml/l.

After extraction of the carbon monoxide, the process of the invention comprises a stage of reduction of the dissolved palladium, generally in the 2+ oxidation state, to palladium in the zero oxidation state (Pd(0)). This palladium is separated from the reaction medium by the usual liquid/solid separating techniques, such as filtration, separation by settling, centrifugation, distillation or evaporation of the liquid medium.

According to a preferred embodiment of the invention, a compound which is insoluble in the reaction medium is present in the said medium before the precipitation of the Pd(0).

This insoluble compound can be added to the reaction medium at any time, for example at the beginning of the hydroxycarbonylation process, at the end of the latter or immediately before the stage of reduction of the palladium.

This insoluble compound is advantageously added before the beginning of the hydroxycarbonylation reaction.

According to the invention, the palladium in the zero oxidation state precipitates and is deposited on or in the heterogeneous phase composed of this insoluble compound, thus facilitating its extraction and its separation from the reaction medium.

Generally, this insoluble compound should not have an effect on the hydroxycarbonylation reaction, in particular should not influence the catalytic effect of the palladium or the selectivity of the reaction.

Mention may be made, as insoluble compounds which are suitable for the invention, of inorganic compounds which are advantageously porous or which exhibit a large specific surface area. Mention may be made, in this family of compounds, as examples, of active charcoals, alumina, silica, zirconia, cerium oxide or more generally rare earth metal oxides.

Mention may be made, as other insoluble compounds which are suitable for the invention, of polymer foams, such as polystyrene foams, or silicone oils.

The amount of insoluble compounds added is not critical and can vary within wide limits.

According to one characteristic of the invention, the stage of reduction of the palladium to the zero oxidation state is carried out by placing the reaction medium under a hydrogen atmosphere.

However, it is also possible, without departing from the scope of the invention, to add a reducing compound to the medium, such as borohydrides, such as $NaBH_4$, for example, or metal hydrides.

This reducing stage can be carried out between ambient temperature (20° C.) and 150° C. and at a hydrogen pressure of between 1 bar and 100 bar.

However, in an embodiment which makes it possible to reduce the palladium to the zero oxidation state without affecting the unsaturation or unsaturations present in the hydrocarbonyl compound, the temperature of the reducing stage is advantageously between 20° C. (ambient temperature) and 80° C.

In the other embodiment, with a temperature of between 80° C. and 150° C., the unsaturations of the. carboxylic acid obtained by hydrocarbonylation can be hydrogenated to obtain a saturated carboxylic acid. The process of the invention thus makes it possible, starting from butadiene, to produce pentanoic acid.

The process of the invention makes it possible to recover all the palladium present in the reaction medium.

In addition, the insoluble compound comprising the palladium can be treated with acids to redissolve the palladium and to make it possible to recycle it in a further hydroxycarbonylation stage.

The process of the invention thus makes it possible to implement the reactions for the hydroxycarbonylation of unsaturated compounds with catalysis with palladium without loss of catalyst. Such a process can thus be operated economically.

The invention will be more fully illustrated by the examples given below, which are solely by way of illustration and without limiting effect.

EXAMPLE 1

The following are charged to a glass flask:

| | |
|---|---|
| 3-Pentenoic acid (90% purity) | 10.0 g |
| Butadiene | 2.7 g (50 mmol) |
| Chlorobutene | 0.3 g (0.35 mmol) |
| Water | 0.9 g (50 mmol) |
| Palladium-on-active-charcoal (3%) | 0.71 g |

This Pd/C catalyst is sold by Engelhard under the trade name Escat 162 5207.

The glass flask is introduced into a 125 ml autoclave. The latter is immediately pressurized to 100 bar of CO at ambient temperature. The autoclave is placed in an oven and the mixture is heated to 140° C. while shaking. When the preset temperature is reached, the CO pressure is raised to 200 bar with connection to a source of CO to maintain a constant pressure. The CO consumption is estimated with respect to the difference in pressure measured in the source.

After reacting for 40 minutes, corresponding to a degree of conversion (DC) of the butadiene of 63%, the autoclave is cooled in a water bath to 20° C. and then degassed. Three purges with hydrogen are carried out under a pressure of 20 bar of hydrogen. The CO content in the medium is 0.6 ml of CO per litre of solution.

A pressure of 20 bar of hydrogen is applied and the mixture is heated at 80° C. with stirring for one hour (phase of reduction of the palladium). After cooling and degassing, the reaction medium is filtered. The charcoal collected is dried before analysis.

The reaction mass collected after filtration is analysed by liquid chromatography (HPLC) and gas chromatography (GC).

The following results were obtained:

CY (3-pentenoic acid)=92%

CY (diacids)=4.6%

CY (2-methyl-3-butenoic acid)=2.9%.

CY (pentanoic acid)=0.07%

Quantitative determination of the palladium on the charcoal collected and in the reaction mass after filtration is carried out by ICP-OES or ICP-MS. The results show that 98% of the palladium charged to the reaction is recovered on the charcoal and 1% is found in the dissolved form in the reaction medium.

The term "degree of conversion (DC) of the butadiene" should be understood as meaning the ratio, expressed as %, of the number of moles of butadiene which have disappeared to the number of moles of butadiene charged.

The term "CY" should be understood as meaning the selectivity for the product X indicated corresponding to the ratio, expressed as %, of the number of moles of product X formed to the number of theoretical moles of product X calculated for the number of moles of butadiene converted.

EXAMPLE 2

The following are charged to a glass flask:

| | |
|---|---|
| 3-Pentenoic acid (90% purity) | 10.0 g |
| Butadiene | 2.6 g |
| Chlorobutene | 0.15 g |
| Water | 0.9 g |
| Palladium acetate | 0.10 g |
| Charcoal, Ceca L3S | 1.1 g |

The charcoal is sold by Ceca.

The glass flask is introduced into a 125 ml autoclave. The latter is immediately pressurized to 100 bar of CO at ambient temperature. The autoclave is placed in an oven and the mixture is heated to 140° C. while shaking. When the preset temperature is reached, the CO pressure is brought to 200 bar and the autoclave is placed in communication with a source of CO to maintain a constant pressure. The CO consumption is estimated with respect to the difference in pressure measured in the source.

After reacting for 19 minutes, corresponding to a DC of the butadiene equal to 65%, the autoclave is cooled in a water bath to 20° C. and then degassed. Two purges with hydrogen are carried out under 20 bar of hydrogen. The solution obtained comprises 40 ml of CO per litre of solution.

A pressure of 20 bar of hydrogen is applied and the mixture is heated at 40° C. with stirring for fifteen minutes. After cooling and degassing, the reaction medium is filtered. The charcoal recovered is dried before analysis. The reaction mass is analysed by high performance liquid chromatography (HPLC) and gas chromatography (GC).

The following results were obtained:

CY (3-pentenoic acid)=83%

CY (diacids)=11%

CY (2-methyl-3-butenoic acid)=3.6%

CY (pentanoic acid)=1.8%

Quantitative determination of the palladium on the charcoal collected and in the reaction mass after filtration is carried out by ICP-OES or ICP-MS. The results show that 1% of the palladium charged to the reaction its found in the dissolved form in the reaction medium, the remainder being recovered on the charcoal.

EXAMPLE 3

The following are charged to a glass flask:

| | |
|---|---|
| 3-Pentenoic acid (90% purity) | 10.0 g |
| Butadiene | 3.2 g |
| Chlorobutene | 0.32 g |
| Water | 0.9 g |
| Palladium acetate | 0.10 g |
| Charcoal, Ceca L3S | 1.0 g |

The charcoal is sold by Ceca.

The glass flask is introduced into an 125 ml autoclave. The latter is immediately pressurized to 100 bar of CO at ambient temperature. The autoclave is placed in an oven and the mixture is heated to 140° C. with shaking. When the preset temperature is reached, the CO pressure is brought to 200 bar and the autoclave is placed in communication with a source of CO to maintain a constant pressure. The CO consumption is estimated with respect to the difference in pressure measured in the source.

After reacting for 23 minutes, corresponding to a DC of the butadiene equal to 70%, the autoclave is cooled in a water bath to 20° C. The autoclave is reduced in pressure and placed under a pressure of 60 bar with an $H_2$/CO mixture with a 95/5 content by weight. The autoclave is heated at 40° C. for 45 minutes. After cooling and degassing, the reaction mixture is filtered. The charcoal recovered is dried before analysis. The reaction mass is analysed by high performance liquid chromatography (HPLC) and gas chromatography (GC).

The following results were obtained:

CY (3-pentenoic acid)=87%

CY (diacids)=10%

CY (pentanoic acid)=0.25%

CY (2-methyl-3-butenoic acid)=3.2%

Quantitative determination of the palladium on the charcoal collected and in the reaction mass after filtration is carried out by ICP-OES or ICP-MS. The results show that only 34% of the palladium charged to the reaction is recovered on the charcoal and 62% is found in the dissolved form in the reaction medium.

EXAMPLE 4

The following are charged to a glass flask:

| | |
|---|---|
| 3-Pentenoic acid (90% purity) | 10.2 g |
| Butadiene | 2.7 g |
| Chlorobutene | 0.20 g |
| Water | 0.9 g |

-continued

| | |
|---|---|
| Palladium-on-active-charcoal (3%) | 1.0 g |

This Pd/C catalyst is sold by Engelhard under the trade name Escat 162 5207

The glass flask is introduced into a 125 ml autoclave. The latter is immediately pressurized to 100 bar of CO at ambient temperature. The autoclave is placed in an oven and the mixture is heated to 140° C. with shaking. When the preset temperature is reached, the CO pressure is brought to 200 bar and the autoclave is placed in communication with a source of CO to maintain a constant pressure. The CO consumption is estimated with respect to the difference in pressure measured in the source.

After reacting for 24 minutes, corresponding to a DC of the butadiene equal to 51%, the autoclave is cooled in a water bath to 20° C. and then slowly degassed. No purging is carried out, the CO concentration being 1000 ml of CO per litre of solution. A pressure of 20 bar of hydrogen is then applied and the mixture is heated at 40° C. with stirring for fifteen minutes. After cooling and degassing, the reaction medium is filtered. The charcoal recovered is dried before analysis. The reaction mass is analysed by high performance liquid chromatography (HPLC) and gas chromatography (GC).

The following results were obtained:

CY (3-pentenoic acid)=87%

CY (diacids)=10%

CY (pentanoic acid)=0.3%

Quantitative determination of the palladium on the charcoal collected and in the reaction mass after filtration is carried out by ICP-OES or ICP-MS. The results show that 88% of the palladium charged to the reaction is found in the dissolved form in the reaction medium.

EXAMPLE 5

The following are charged to a glass flask:

| | |
|---|---|
| 3-Pentenoic acid (90% purity) | 10.0 g |
| Butadiene | 2.7 g |
| Chlorobutene | 0.30 g |
| Water | 0.9 g |
| Palladium acetate | 0.11 g |
| Charcoal, Ceca L3S | 1.0 g |

The glass flask is introduced into a 125 ml autoclave. The latter is immediately pressurized to 100 bar of CO at ambient pressure. The autoclave is placed in an oven and the mixture is heated to 140° C. with shaking. When the preset temperature is reached, the CO pressure is brought to 200 bar and the autoclave is placed in communication with a source of CO to maintain a constant pressure. The CO consumption is estimated with respect to the difference in pressure measured in the source.

After reacting for 14 minutes, corresponding to a DC of the butadiene equal to 64%, the autoclave is cooled in a water bath to 20° C. and then slowly degassed. No purging is carried out. A pressure of 20 bar of hydrogen is then applied and the mixture is heated at 80° C. with stirring for fifteen minutes. After cooling and degassing, the reaction medium is filtered. The charcoal recovered is dried before analysis. The reaction mass is analysed by high performance liquid chromatography (HPLC) and gas chromatography (GC).

The following results were obtained:

CY (3-pentenoic acid)=80%

CY (diacids)=15%

CY (pentanoic acid)=0.2%

CY (2-methyl-3-butenoic acid)=3.8%

Quantitative determination of the palladium on the charcoal collected and in the reaction mass after filtration is carried out by ICP-OES or ICP-MS. The results show that 80% of the palladium charged to the reaction is found in the dissolved form in the reaction medium.

EXAMPLE 6

The following are charged to a glass flask:

| | |
|---|---|
| 3-Pentenoic acid (90% purity) | 10.0 g |
| Butadiene | 2.6 g |
| Chlorobutene | 0.30 g |
| Water | 0.91 g |
| Palladium acetate | 0.10 g |
| Charcoal, Ceca L3S | 1.0 g |

The glass flask is introduced into a 125 ml autoclave. The latter is immediately pressurized to 100 bar of CO at ambient pressure. The autoclave is placed in an oven and the mixture is heated to 140° C. with shaking. When the preset temperature is reached, the CO pressure is brought to 200 bar and the autoclave is placed in communication with a source of CO to maintain a constant pressure. The CO consumption is estimated with respect to the difference in pressure measured in the source.

At the end of the reaction, the autoclave is cooled in a water bath to 20° C. and then slowly degassed. Purging is carried out with 40 bar of hydrogen and the CO concentration falls to 40 ml of CO per litre of solution. A pressure of 20 bar of hydrogen is then applied and the mixture is heated at 40° C. with stirring for fifteen minutes. After cooling and degassing, the reaction medium is filtered. The charcoal recovered is dried before analysis. The reaction mass is analysed by high performance liquid chromatography (HPLC) and gas chromatography (GC).

The following results were obtained:

CY (3-pentenoic acid)=80%

CY (diacids)=12%

CY (pentanoic acid)=2.1%

CY (2-methyl-3-butenoic acid)=3.9%

Quantitative determination of the palladium on the charcoal collected and in the reaction mass after filtration is carried out by ICP-OES or ICP-MS. The results show that 1% of the palladium charged to the reaction is found in the dissolved form in the reaction medium.

EXAMPLE 7

The following are charged to a glass flask:

| | |
|---|---|
| 3-Pentenoic acid (90% purity) | 10.0 g |
| Butadiene | 2.8 g |
| Chlorobutene | 0.31 g |
| Water | 0.9 g |
| Palladium acetate | 0.10 g |
| Charcoal, Ceca L3S | 1.0 g |

The charcoal is sold by Ceca.

The glass flask is introduced into a 125 ml autoclave. The latter is immediately pressurized to 100 bar of CO at ambient temperature. The autoclave is placed in an oven and the mixture is heated to 140° C. with shaking. When the preset temperature is reached, the CO pressure is brought to 200 bar and the autoclave is placed in communication with a source of CO to maintain a constant pressure. The CO consumption is estimated with respect to the difference in pressure measured in the source.

At the end of the reaction, the autoclave is cooled in a water bath to 20° C. The autoclave is reduced in pressure, then three purges with hydrogen are carried out under 20 bar of hydrogen (the CO concentration falling to 0.6 ml per litre of solution), then a pressure of 10 bar of hydrogen is applied and the mixture is heated at 80° C. with stirring for five minutes. After cooling and degassing, the reaction medium is filtered. The charcoal recovered is dried before analysis. The reaction mass is analysed by high performance liquid chromatography (HPLC) and gas chromatography (GC).

The following results were obtained:

CY (3-pentenoic acid)=81%

CY (4-pentenoic acid)=3.7%

CY (diacids)=8.5%

CY (2-methyl-3-butenoic acid)=3.3%

CY (pentanoic acid)=4.4%

Quantitative determination of the palladium on the charcoal collected and in the reaction mass after filtration is carried out by ICP-OES or ICP-MS. The results show that 97% of the palladium charged to the reaction is recovered on the charcoal and 1% is found in the dissolved form in the reaction medium.

EXAMPLE 8

The following are charged to a glass flask:

| | |
|---|---|
| 3-Pentenoic acid (90% purity) | 10.0 g |
| Butadiene | 2.7 g |
| Chlorobutene | 0.30 g |
| Water | 0.95 g |
| Palladium acetate | 0.10 g |
| Alumina, Degussa type C | 1.0 g |

The glass flask is introduced into a 125 ml autoclave. The latter is immediately pressurized to 100 bar of CO at ambient temperature. The autoclave is placed in an oven and the mixture is heated to 140° C. with shaking. When the preset temperature is reached, the CO pressure is brought to 200 bar and the autoclave is placed in communication with a source of CO to maintain a constant pressure. The CO consumption is estimated with respect to the difference in pressure measured in the source.

At the end of the test, the autoclave is cooled in a water bath to 20° C. and then degassed. Three purges with hydrogen are carried out under 20 bar of hydrogen (the CO concentration falling to 0.6 ml per litre of solution), then a pressure of 20 bar of hydrogen is applied and the mixture is heated at 80° C. with stirring for forty-five minutes. After cooling and degassing, the reaction medium is filtered. The alumina recovered is dried before analysis.

Quantitative determination of the palladium on the alumina collected and in the reaction mass after filtration is carried out by ICP-OES or ICP-MS. The results show that 97% of the palladium charged to the reaction is recovered on the alumina and less than 0.05% is found in the dissolved form in the reaction medium.

EXAMPLE 9

1) Preparation of the π-crotyl-Pd Chloride Complex 5.04 g of $PdCl_2$, 3.37 g of NaCl, 50 $cm^3$ of methanol, 15 $cm^3$ of water, 8.03 g of crotyl chloride and a further 20 $cm^3$ of methanol are successively charged to a 150 $cm^3$ round-bottomed glass flask.

The heterogeneous mixture is stirred and becomes gradually dark brown and cloudy. The solution is subsequently treated with stirring with a gentle stream of carbon monoxide (bubble by bubble) for one hour. The mixture becomes clearer and a yellow precipitate appears. The stirring and the stream of CO are halted, the solution is left standing for one hour and then it is poured into 300 $cm^3$ of water and extracted with 5 times 50 $cm^3$ of chloroform. The resulting straw-yellow organic phase is washed with 2 times 100 $cm^3$ of water and dried over disodium sulphate overnight, and then the solvent is evaporated. 3.35 g of a pale yellow solid are thus recovered, the solid having a purity of greater than 94% (quantitative determination by Nuclear Magnetic Resonance: NMR).

2) Hydroxycatbonylation of Chlorobutene

The following are charged to a glass flask:

| | |
|---|---|
| Chlorobutene | 5.0 g |
| Chlorocrotyl palladium | 10.3 mg |

The glass flask is introduced into a 125 ml autoclave. The latter is immediately pressurized to 100 bar of CO at ambient temperature. The autoclave is placed in an oven and the mixture is heated to 130° C. with shaking. When the preset temperature is reached, the CO pressure is brought to 200 bar and the autoclave is placed in communication with a source of CO to maintain a constant pressure.

After 60 minutes, the autoclave is cooled in a water bath to 20° C. and then degassed. The homogeneous reaction mass is analysed by high performance liquid chromatography (HPLC) and gas chromatography (GC).

The following results were obtained:

RY (P3)=12.7%

RY (P2)=4.4%

The remainder is very predominantly chlorobutene.

2.09 g of the solution thus obtained are placed in a glass flask and 95 mg of Ceca L3S charcoal are added. Two purges under 15 bar of hydrogen are carried out and the mixture is shaken under 20 bar of $H_2$ and heated to 80° C. Once the temperature has been reached, a pressure of 40 bar of hydrogen is applied for 60 minutes. The autoclave is degassed and the reaction medium is filtered.

Quantitative determination of the palladium on the charcoal collected and in the reaction mass after filtration is carried out by ICP-OES or ICP-MS. The results show that 100% of the palladium charged to the reaction is recovered on the charcoal.

EXAMPLE 10

The following are charged to a glass flask:

| | |
|---|---|
| Pentanoic acid | 10.0 g |
| Butadiene | 2.6 g |
| Chlorobutene | 0.30 g |
| Water | 0.92 g |
| Palladium acetate | 0.11 g |
| Charcoal, Ceca L3S | 1.0 g |

The glass flask is introduced into a 125 ml autoclave. The latter is immediately pressurized to 100 bar of CO at ambient temperature. The autoclave is placed in an oven and the mixture is heated to 140° C. with shaking. When the preset temperature is reached, the CO pressure is brought to 200 bar and the autoclave is placed in communication with a source of CO to maintain a constant pressure. The CO consumption is estimated with respect to the difference in pressure measured in the source.

At the end of the reaction, the autoclave is cooled in a water bath to 20° C. and then slowly degassed. Five purges are carried out under 60 bar of hydrogen (the CO concentration falling to 0.05 ml per litre of solution). The mixture is then heated at 140° C. under 70 bar of hydrogen with stirring for thirty-five minutes. After cooling and degassing, the reaction medium is filtered. The charcoal recovered is dried before analysis. The reaction mass is analysed by high performance liquid chromatography (HPLC) and gas chromatography (GC).

The following results were obtained:

CY (pentanoic acid)=93%

CY (diacids)=3.0%

CY (2-methyl-3-butanoic acid)=3.9%

Quantitative determination of the palladium on the charcoal collected and in the reaction mass after filtration is carried out by ICP-OES or ICP-MS. The results show that nearly 100% of the palladium charged to the reaction is recovered on the charcoal, 0.025% being found in the dissolved form in the reaction medium.

What is claimed is:

1. Process for the preparation of unsaturated or saturated carboxylic acids from compounds comprising an ethylenic or acetylenic unsaturation conjugated with an other unsaturation or an electron-donating group by hydroxycarbonylation reaction with carbon monoxide and water in the presence of a palladium-based catalyst in a reaction medium, which comprises (1) treating the reaction medium comprising said unsaturated or unsaturated carboxylic acids, byproducts, and water, after the end of the hydroxycarbonylation reaction, with a gas to extract carbon monoxide from the reaction medium to obtain a CO concentration in the reaction medium of less than 600 ml of CO per litre, (2) treating the reaction medium with hydrogen to reduce the palladium to the zero oxidation state, and (3) separating precipitated palladium from the reaction medium.

2. Process according to claim 1, wherein the concentration of carbon monoxide in the reaction medium before the stage of treatment with hydrogen is less than 10 mmol/1.

3. Process according to claim 2, wherein the concentration of carbon monoxide in the reaction medium before the stage of treatment with hydrogen is between 0.001 ml/l and 600 ml/l.

4. Process according to claim 1, wherein the gas for entrainment of the carbon monoxide is selected from the group consisting of nitrogen, the rare gases and hydrogen.

5. Process according to claim 1, wherein the stage of reduction of the palladium to the zero oxidation state is carried out under a hydrogen pressure of between 1 bar and 100 bar.

6. Process according to claim 1, wherein the stage of reduction of the palladium to the zero oxidation state is carried out at a temperature of between 20° C. and 150° C.

7. Process according to claim 1, wherein a compound which is insoluble in the reaction medium is added to the said medium and then separated from the said medium after the stage of reduction of the palladium to the zero oxidation stage.

8. Process according to claim 7, wherein the compound which is insoluble in the reaction medium is selected from the group consisting of active charcoals, alumina, silica, zirconia, cerium oxide, polystyrene foams and silicone oils.

9. Process according to claim 7, wherein the compound which is insoluble in the reaction medium is added at the beginning of the reaction.

10. Process according to claim 7, wherein the compound which is insoluble in the reaction medium is added before the stage of reduction of the palladium.

11. Process according to claim 1, wherein the compounds comprising a conjugated ethylenic unsaturation are selected from the group consisting of diolefins, allyl alcohols, allyl ethers, allyl esters and allyl halides.

12. Process according to claim 11, wherein the diolefin is butadiene.

13. Process according to claim 7, wherein the palladium deposited on the insoluble compound is recovered by treatment of the said insoluble compound after separation from the reaction medium.

14. Process according to claim 13, wherein the treatment of the insoluble compound comprising the reduced palladium is a dissolution of the palladium by attack by a strong acid.

* * * * *